(12) United States Patent
Larsen et al.

(10) Patent No.: US 7,797,990 B2
(45) Date of Patent: Sep. 21, 2010

(54) DISPOSABLE CARTRIDGE FOR CHARACTERIZING PARTICLES SUSPENDED IN A LIQUID

(75) Inventors: Ulrik Darling Larsen, Holte (DK); Preben Merrild Elkjær, Copenhagen (DK)

(73) Assignee: Chempaq A/S, Copenhagen O (DK)

( * ) Notice: Subject to any disclaimer, the term of this patent is extended or adjusted under 35 U.S.C. 154(b) by 705 days.

(21) Appl. No.: 10/517,382

(22) PCT Filed: Jun. 11, 2003

(86) PCT No.: PCT/DK03/00384

§ 371 (c)(1),
(2), (4) Date: May 24, 2005

(87) PCT Pub. No.: WO03/104770

PCT Pub. Date: Dec. 18, 2003

(65) Prior Publication Data

US 2005/0214928 A1    Sep. 29, 2005

Related U.S. Application Data

(60) Provisional application No. 60/387,407, filed on Jun. 11, 2002.

(30) Foreign Application Priority Data

Feb. 5, 2003    (DK) ................................ 2003 00159

(51) Int. Cl.
*G01N 15/06*    (2006.01)
(52) U.S. Cl. ..................................................... 73/61.71

(58) Field of Classification Search ................. 324/71.4; 73/61.71
See application file for complete search history.

(56) References Cited

U.S. PATENT DOCUMENTS

| | | |
|---|---|---|
| 2,656,508 A | 10/1953 | Coulter |
| 3,122,431 A | 2/1964 | Coulter et al. |
| 3,395,343 A | 7/1968 | Morgan et al. |
| 3,549,994 A | 12/1970 | Rothermel et al. |
| 3,902,115 A | 8/1975 | Hogg et al. |

(Continued)

FOREIGN PATENT DOCUMENTS

EP    0193394 B1    7/1991

(Continued)

OTHER PUBLICATIONS

Volker Kachel, "Electrical Resistance Pulse Sizing: Coulter-Sizing", Flow Cytometry and Sorting, pp. 45-80, 2nd ed., 1990 Wiley-Liss Inc.

(Continued)

*Primary Examiner*—Hezron Williams
*Assistant Examiner*—Mark Shabman
(74) *Attorney, Agent, or Firm*—Volentine & Whitt, P.L.L.C.

(57) ABSTRACT

A particle characterization apparatus in which particles suspended in a liquid pass through an orifice or aperture for detection and characterization of the particles utilizing impedance determination. In particular, the apparatus includes a membrane of a polymer as a base material for precision machining of a sub-millimeter orifice. Forming the orifice in a polymer membrane facilitates the construction of a single use cartridge for haematology analysis due to low material and production costs.

29 Claims, 9 Drawing Sheets

U.S. PATENT DOCUMENTS

Figure 1:
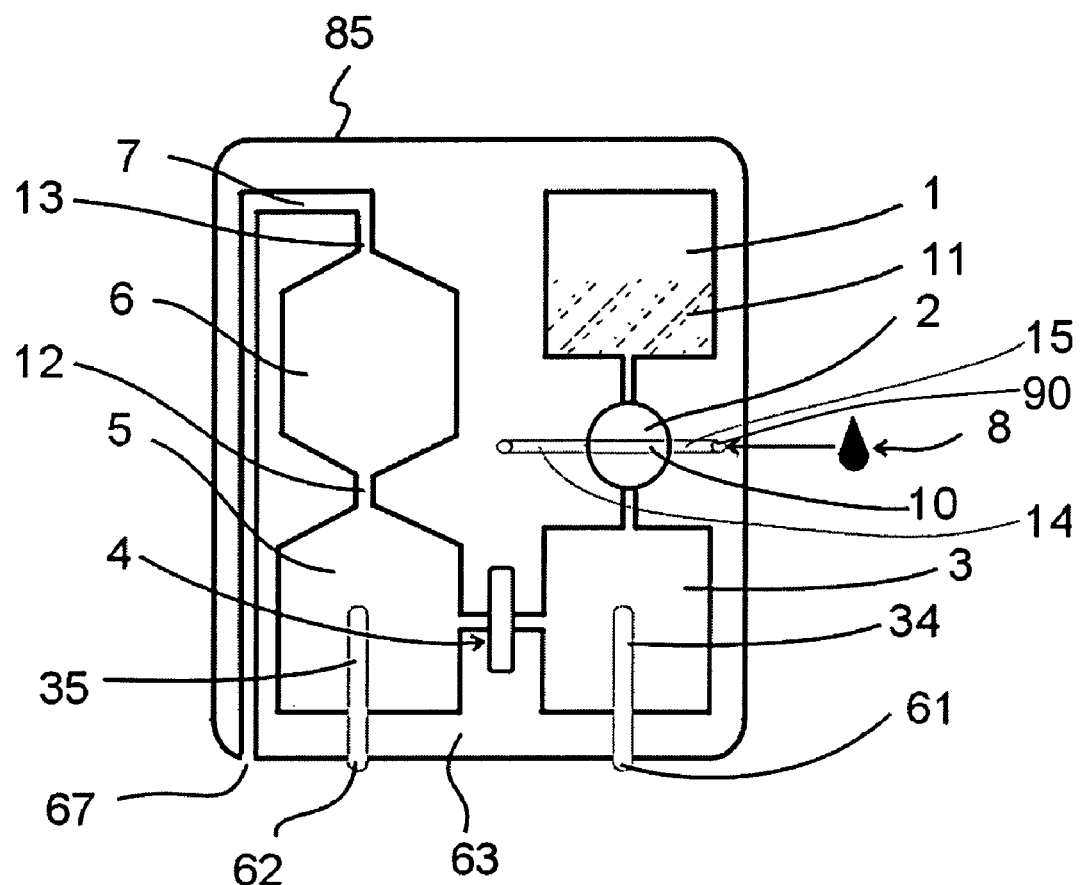

| | | | |
|---|---|---|---|
| 3,958,177 A | 5/1976 | Reeves et al. | |
| 4,014,611 A | 3/1977 | Simpson et al. | |
| 4,346,018 A | 8/1982 | Carter et al. | |
| 4,485,175 A | 11/1984 | Ledis et al. | |
| 4,521,729 A * | 6/1985 | Kiesewetter et al. | 324/71.1 |
| 4,528,274 A | 7/1985 | Carter et al. | |
| 4,600,880 A | 7/1986 | Doutre et al. | |
| 4,607,526 A | 8/1986 | Bachenheimer et al. | |
| 4,706,207 A | 11/1987 | Hennessy et al. | |
| 4,738,827 A | 4/1988 | Pierotti | |
| 4,745,071 A | 5/1988 | Lapicola et al. | |
| 4,751,179 A | 6/1988 | Ledis et al. | |
| 4,760,328 A | 7/1988 | Groves | |
| 4,835,457 A * | 5/1989 | Hanss et al. | 324/71.4 |
| 4,926,114 A | 5/1990 | Doutre | |
| 4,962,038 A | 10/1990 | Carter et al. | |
| 5,045,474 A | 9/1991 | Becker et al. | |
| 5,077,017 A | 12/1991 | Gorin et al. | |
| 5,104,813 A | 4/1992 | Besemer et al. | |
| 5,198,749 A | 3/1993 | Guthrie et al. | |
| 5,230,866 A | 7/1993 | Shartle et al. | |
| 5,231,005 A | 7/1993 | Russell et al. | |
| 5,241,262 A | 8/1993 | Guthrie et al. | |
| 5,257,984 A | 11/1993 | Kelley | |
| 5,316,951 A | 5/1994 | Carver, Jr. et al. | |
| 5,334,502 A | 8/1994 | Sangha | |
| 5,348,859 A | 9/1994 | Brunhouse et al. | |
| 5,393,496 A | 2/1995 | Seymour | |
| 5,500,992 A | 3/1996 | Barnes et al. | |
| 5,501,982 A | 3/1996 | Saldivar, Jr. et al. | |
| 5,623,200 A | 4/1997 | Ogino | |
| 5,716,852 A | 2/1998 | Yager et al. | |
| 5,731,206 A | 3/1998 | Ledis et al. | |
| 5,763,280 A | 6/1998 | Li et al. | |
| 5,804,022 A | 9/1998 | Kaltenbach et al. | |
| 5,834,315 A | 11/1998 | Riesgo et al. | |
| 5,840,515 A | 11/1998 | Provost | |
| 5,911,871 A | 6/1999 | Preiss et al. | |
| 5,979,251 A | 11/1999 | James et al. | |
| 6,111,398 A * | 8/2000 | Graham | 324/71.4 |
| 6,230,896 B1 | 5/2001 | Lambert | |
| 6,251,615 B1 | 6/2001 | Oberhardt | |
| 6,319,209 B1 | 11/2001 | Kriz | |
| 6,387,328 B1 | 5/2002 | Berndtsson | |
| 6,663,833 B1 | 12/2003 | Stave et al. | |

FOREIGN PATENT DOCUMENTS

| | | |
|---|---|---|
| EP | 0 549 414 A1 | 12/1992 |
| EP | 0 844 475 A2 | 11/1997 |
| EP | 1 182 457 A1 | 8/2000 |
| GB | 2 232 769 A | 12/1990 |
| GB | 2232769 A | 12/1990 |
| GB | 1002424 B | 8/1996 |
| GR | 1 002 424 | 8/1996 |
| JP | 5915849 A | 1/1984 |
| JP | 61205844 | 9/1986 |
| JP | 7301595 | 11/1995 |
| JP | 8015125 | 1/1996 |
| JP | 9304265 | 11/1997 |
| JP | 2002515601 | 5/2002 |
| WO | WO 93/01306 | 1/1993 |
| WO | WO 97/24600 | 7/1997 |
| WO | WO 98/54568 | 3/1998 |
| WO | WO 98/50777 | 11/1998 |
| WO | WO 99/01742 | 1/1999 |
| WO | WO 9901742 A1 * | 1/1999 |
| WO | WO 99/49319 | 9/1999 |
| WO | 9960379 | 11/1999 |
| WO | WO 00/07254 | 2/2000 |
| WO | WO 00 07254 A | 2/2000 |
| WO | WO 01/11338 A1 | 2/2001 |
| WO | WO 01/69292 A2 | 9/2001 |
| WO | WO 02/089670 A1 | 11/2002 |

OTHER PUBLICATIONS

Ed. M.M. Wintrobe et al., "Clinical Hematology", pp. 3-9, 1981, 8th ed., Lea & Febiger, Philadelphia, USA.

M. Madou, "Fundamenetals of Microfabrication", pp. 29-32, 66-70, 145, and 163-164, CRC Press LLC, 1997, ISBN 0-8493-9451-1.

Stevens, "Fundamentals of Clinical Hematology", pp. 6-7, and 301-304, W.B. Saunders Company, ISBN 0-7216-4177-6, Philadelphia, USA.

A.Y. Fu et al., "A Microfabricated fluorescene-activated cell sorter", Nature Biotechnology, vol. 17, Nov. 1999, pp. 1109-1111.

B.K. Gale et al., Micromachined Electrical Field-Flow Fractionation (u-EFFF) System:, Proceedings of the IEEE Annual International Workshop; pp. 119-124; Jan. 1997.

* cited by examiner

DISPOSABLE CARTRIDGE FOR CHARACTERIZING PARTICLES SUSPENDED IN A LIQUID

CROSS REFERENCE TO RELATED APPLICATIONS

This application claims priority under 35 U.S.C. 119 to Danish application PA 2003 00159 filed on Feb. 5, 2003, and under 35 U.S.C. 119(e)(1) to U.S. Provisional application Ser. No. 60/387,407 filed Jun. 11, 2002, which are hereby incorporated by reference.

The present invention relates to a particle characterization apparatus in which particles suspended in a liquid passes through an orifice or aperture for detection and characterization of the particles utilising impedance determination. In particular the invention relates to utilisation of a membrane of a polymer as a base material for precision machining of a sub-millimetre orifice. Forming the orifice in a polymer membrane facilitates the construction of a single use cartridge for haematology analysis due to low material and production costs.

Automated Blood Analysers (Haematology Analysers) are based on electrical or optical ways of characterizing each individual blood cell on the fly in a fluid flow. Such instrumentation is rather sophisticated and requires trained personnel to perform the measurements. Counting and sizing of particles by impedance cell sizing, also known as Coulter Sizing or Coulter counting (see V. Kachel, "Electrical Resistance Pulse Sizing: Coulter Sizing", Flow Cytometry and Sorting, Second Edition, pp. 45-80, 1990 Wiley-Liss), is a broadly accepted method that is being used in most haematology-analysers and particle counting equipment. The method is based on measurable changes in the electrical impedance produced by comparatively non-conductive particles in an electrolyte. A small opening called the "aperture" or "orifice" connects two electrically isolated chambers, each having electrodes for contacting the electrolyte. The orifice works as a restriction to the electrical path, whereby a sensing zone is established through which the particles are aspirated. In the sensing zone each particle will give rise to a displacement of the surrounding electrolyte, thus blocking part of the current-path and giving rise to a short voltage pulse. By aspiration of particles one by one through the orifice, the particles can be characterized with respect to volume and conductivity by registration of the pulse characteristics. The concentration of specific subgroups of the particles may be determined from the pulse characteristics and by metering the analysed sample volume.

Conventional instruments utilizing the impedance technique are based on a fixed membrane with a precision-machined orifice, which is being maintained by flushing and rinsing the membrane. In conventional impedance cell-sizing equipment, the orifice is made in a membrane of sapphire by micro drilling and polishing. These orifices show excellent robustness and may be used repeatedly for several thousand analyses when cleaned properly in between. However, being made of sapphire and requiring cumbersome techniques of preparation, these membranes are fairly expensive to replace.

WO 01/69292 discloses a portable haematology analyser with a maintenance-free reader and a unique disposable cartridge for blood sampling and handling. The disposable cartridge includes a membrane with an orifice for impedance cell sizing.

In order to be able to provide single-use cartridges, there is a need for a cheap, single-use membrane material with a precision-machined orifice.

Further, there is a need for a method of producing a membrane with an orifice with accuracy and reproducibility at low cost Typically, the known methods do not provide the required accuracy. In order to facilitate accurate impedance determination, it is desired that the accuracy of the diameter of the orifice lie within +/−10%, more preferably within +/−5% and more preferably within +/−2%. The desired diameter of the orifice is typically in the range from 10 µm to 1000 µm, preferably in the range from 30 µm to 75 µm. Thus, the manufacturing process must therefore be able to provide orifices with a precision in the µm-scale, e.g. within +/−2 µm accuracy in order for the manufactured membrane with orifice to provide useful results.

Thus, it is an object of the present invention to provide a membrane with an orifice for use in an Impedance cell sizing apparatus, e.g. with a single-use cartridge, for characterizing particles suspended in a liquid, e.g. cells in a blood sample. Preferably, the cartridge enables sample taking, sample preparation, and particle characterization so that analysis may be performed within one device without a need for sample handling and sample transfer to another unit.

The single-use cartridge is intended to be discarded after analysis of one liquid sample.

According to the present invention, the above-mentioned and other objects are fulfilled by a method of producing an orifice in a polymer membrane by precision machining, such as milling, drilling, punching, ablation, evaporation, injection moulding, punching, water cutting, air cutting, laser cutting, etc.

The use of a polymer sheet has proved to be the ideal way of meeting the request for a disposable cartridge for cell analysis. The major advantages of the polymer sheet are the low cost of the material, the low cost of the manufacturing process, simple and reliable welding methods with other polymers, ideal electrical insulation characteristics and good chemical stability.

Soft polymers, such as photopolymers (photoresist), are soft or fluid in nature and must be applied on a supporting surface before hardening. The membrane thickness of such photopolymers is difficult to control and may vary significantly over the entire surface on which it has been applied. In order to yield control of the thickness over a larger area of the membrane, the membrane must be fabricated by using rolls to define the required thickness.

Thus, preferably, the polymer membrane is manufactured from a hardened polymer or a hard polymer so that the membrane is self-sustained.

Photolithography is a slow process with many different process steps such as pre-heating, exposure, curing and dissolving, which makes this fabrication method cumbersome and expensive.

Thus, preferably, the precision machining of the membrane comprises other processes than photolithography.

Manufacturing of polymer membranes with orifices by laser cutting according to the present invention provides cheap and rapid production of membranes with precision-machined orifices for impedance particle counting and/or sizing.

The high-energy laser spot causes vaporization or ablation of the material in the focused region of the spot. The laser spot of an excimer laser may be focused to a few micrometers, providing the desired accuracy in accordance with the present invention.

Preferably, the laser is a UV-laser because of its superior laser cutting accuracy.

Preferably, the UV-laser is an excimer laser with a wavelength in the range from 150 nm to 350 nm.

According to one embodiment of the invention, the laser is used like a conventional drill, i.e. the focussed laser spot remains at the desired position of the orifice and the orifice are produced by a series of laser pulses.

According to another embodiment of the invention, the focussed laser beam is scanned along the desired circumference of the orifice thereby cutting-out the orifice of the membrane. In this way any desired circumferential shape of the orifice may be manufactured.

According to yet another embodiment of the invention, a narrow laser beam is scanned for example linearly, e.g. line by line, across the surface of the membrane desired to be removed for creation of the orifice.

According to a second aspect of the invention, a polymer membrane is provided with an orifice with rounded edges at one of the sides of the membrane whereby perturbations of an electrical field at the orifice entrance are minimised and a substantially homogenous electrical field at the centre of the orifice may be provided.

Hereby, electrical pulses generated by particles passing the orifice at the centre of the orifice and particles passing the orifice close to an edge of the orifice will generate substantially identical pulses. Without rounded edges, particles passing the orifice close to an edge will generate a distorted pulse.

Preferably, the radius of curvature of the rounded edges corresponds to ¼th of the diameter of the orifice with a length to diameter ratio of 1. Hereby, a homogeneous field is still reached in the orifice with no field distortion at the edge.

In order to establish the rounded edges of the orifice, the laser is programmed to process a larger area in the beginning and then narrowed down to the diameter defining the effective diameter of the orifice.

Further, a polymer membrane is provided with an orifice with a surface roughness of its internal surface in the range from 0 μm to 5 μm whereby a substantially homogenous electrical field at the centre of the orifice may be provided.

Still further, a polymer membrane is provided with an orifice with a deviation of the orifice diameter along a longitudinal axis of the orifice in the range from +/−1% to +/−10% whereby a substantially homogenous electrical field at the centre of the orifice may be provided.

The membrane according to the present invention may for example be incorporated into a cartridge for characterizing particles suspended in a liquid, comprising a housing with a mixing chamber and a collection chamber separated by the membrane containing the orifice for passage of the particles between the mixing chamber and the collection chamber. Particle characterization means are provided for characterizing particles passing through the orifice.

Sample taking may be performed through a bore in the outer surface of the housing for entrance of a liquid sample. The housing further comprises a sampling member that is movably positioned in the housing. The sampling member has a cavity for receiving and holding a small and precise volume of liquid. In a first position of the sampling member, the cavity is in communication with the bore for entrance of the liquid sample into the cavity, and, in a second position of the sampling member, the cavity is in communication with an inlet to the mixing chamber.

Thus, the sampling member operates to receive and hold a precise volume of liquid sample and to transfer the sample to the inlet of the mixing chamber.

Preferably, liquid to be sampled enters the cavities by capillary attraction causing a liquid flow. Utilization of capillary forces simplify the flow system, since no pumps, membranes, syringes or other flow generating means are needed to take the sample.

Thus, the bore may form a first capillary tunnel for entrance of a liquid sample by capillary attraction. The capillary tunnel is dimensioned so that, upon contact between the bore and liquid to be sampled, a sample of the liquid is drawn into the bore by capillary attraction.

Further, the cavity may form a second capillary tunnel adapted for drawing the liquid sample into the cavity by capillary attraction. Preferably, the first and second capillary tunnel has the same diameter, and it is also preferred that, in the first position, the first and second capillary tunnel extend along substantially the same longitudinal centre axis.

Preferably, the sampling member is rotatable about an axis of rotation that is substantially perpendicular to a longitudinal axis of the cavity.

Additionally or alternatively, the sampling member may be displaced in a direction substantially perpendicular to a longitudinal axis of the cavity.

The surface of the first and second inner capillary tunnel walls may be hydrophilic whereby the capillary attraction of the liquid sample is facilitated. For example, the inner tunnel walls may be made of e.g. glass or polymers, such as polystyrene.

Alternatively, the capillary tunnel walls may be made of another type of material and covalently or non-covalently coated with a hydrophilic material, such as a polymer or a reagent.

The capillary tunnel may also include one or more reagents adhered or chemically bonded to the inner tunnel wall. These reagents serve the purposes of further facilitating the capillary attraction of the sample and optionally also causing a chemical reaction in the liquid sample, e.g. introducing anticoagulant activity in a blood sample. Such reagents may comprise heparin, salts of EDTA, etc.

Preferably, the sampling member is made of a polymer.

In accordance with a further aspect of the invention, an apparatus is provided for characterizing particles suspended in a liquid, comprising a cartridge as disclosed herein, and a docking station for removably receiving the cartridge, the docking station comprising connectors for operational connection with the particle characterization means when the cartridge is received in the docking station.

The cartridge may further comprise a cartridge port communicating with the collection chamber for causing a liquid flow through the orifice, and the docking station may further comprise a corresponding port for forming a gas connection with the cartridge port when the cartridge is received in the docking station for application of a pressure causing a liquid flow through the orifice.

The particle characterization means may include a first electrode in the mixing chamber and a second electrode in the collection chamber, each electrode being electrically connected to a respective terminal member accessible at the outer surface of the cartridge for operational connection to the respective connector of the docking station when the cartridge is received in the docking station. Generally, it is preferred that all necessary electrical and fluid connections to the cartridge can be established by fitting the cartridge into the docking station, preferably by a simple push fit.

The first and second electrodes may facilitate particle characterization utilizing the well-known Coulter impedance principle, e.g. for counting and sizing of blood cells. This method has become a globally accepted method and is being used in the majority of haematology-analysers. Several thousand particles per second may be characterized with high precision and accuracy utilizing this principle.

With the electrical impedance technique it is possible to resolve the particle volume from the measurement. By maintaining a constant current across the orifice, the recorded voltage pulse from particles displacing the electrolyte in the orifice will have a height proportional to the volume of the particle provided that the particles can be considered non-conducting compared to the electrolyte, the electrical field (DC or RF) in the centre of the orifice can be considered homogeneous, which typically is fulfilled when the diameter D is smaller than the length l of the orifice (l/D>1), the particle d can be considered small compared to the diameter of the orifice (d<0.2*D), and that only one particle passes through at a time and the particles are passed through the orifice in along the length of the orifice.

Preferably, the length or depth of the orifice is from 1 to 1000 µm, for example about 50 µm. Desirably the length of the orifice is chosen such that only one particle will be present in the orifice at the time when detecting particles of from 0.1 to 100 µm diameter. However, considerations to the homogeneity of the electrical field in the orifice may require a length of the orifice larger or equal to the diameter. The counts, of which some may be simultaneous counting of two particles, can be corrected mathematically by implementing a statistical estimation. The aspect ratio of the orifice, (length or depth divided by diameter) is preferably from 0.5:1 to 5:1, more preferably from 1:1 to 3:1.

Preferably, the largest cross-sectional dimension of the orifice is from 5 to 200 µm, for example 10 to 50 µm.

The cartridge may further comprise a breather inlet/outlet communicating with the surroundings for preservation of substantially ambient atmospheric pressure in the cartridge flow system for facilitation of liquid flow through the orifice.

Preferably, the cartridge is designed to be disposable after a single use. It is desirable that after use there is no need to clean the apparatus before it can be used in a new assay procedure with a new cartridge. Accordingly, escape of liquid from the cartridge at its entry into the docking station should be avoided. To this end the positioning of the orifice with respect to the breather inlet/outlet, the second chamber inlet/outlet and the particle characterization device components is preferably such that a volume of liquid sufficient for the desired particle characterization can be drawn or pumped through the orifice without the liquid passing out of the housing. Generally, it should be possible to pass a volume of liquid, which is at least 0.1 ml to 10 ml, e.g. 0.5 ml, through the orifice whilst particle characterization measurements are being made with no liquid leaving the cartridge.

The cartridge may comprise volume-metering means for determining the beginning and end of a period during which a predetermined volume of liquid has passed through the orifice.

Preferably, the volume metering means comprises a volume-metering chamber with an input communicating with the collection chamber and an output, and wherein presence of liquid is detected at the input and at the output, respectively.

For example, presence of liquid may be detected optically due to changed optical properties of a channel configuration from being filled with air till when it is being filled with liquid. This could be constructed as reflectance or transmittance detection from the surface, where incident light is reflected from an empty channel and transmitted through a filled channel, thus giving a clear shift in the detected reflected or transmitted light.

It is preferred that the input and output of the metering chamber is formed by narrow channels for accommodation of only a small liquid volume compared to the volume of the metering chamber so that the actual positioning of the volume metering means, e.g. optical reflectance detection, in the channels do not substantially influence the accuracy of the volume metering means determination.

The mixing chamber or the collection chamber may constitute the volume metering chamber; however, it is preferred to provide an independent volume metering chamber facilitating positioning of the volume metering means, e.g. the optical reflectance detection.

The volume metering means may be positioned for sensing when liquid in the metering chamber is at or above respective levels in the volume-metering chamber.

The volume metering means may be used for sensing when the level of the liquid is such that the respective metering means are or are not filled with the liquid and may therefore serve for determining the beginning and end of a period during which a fixed volume of liquid has passed through the orifice. For example, particle characterization may begin when the level of the liquid just rises over the level of a metering means and may end when the level of the liquid just rises over a second metering means, the volume of liquid passing through the orifice during this period being defined by the separation of the respective metering means.

Where the end point of the passage of a defined volume of liquid is the effective emptying of one chamber to below the level of the orifice, it is preferred that each of the collection and mixing chambers (or at least that chamber from which liquid passes) has a transverse cross sectional area at the level of the orifice which is substantially less than the transverse cross sectional area of the chamber over a substantial part of the height of the chamber above the orifice.

When using the Coulter principle the diluent for use in the apparatus according to the invention may contain inorganic salts rendering the liquid a high electrical conductivity. When sample is applied to the electrolyte, the electrolyte to sample volumes should preferably be higher than 10. Sample preparation should preferably result in between 1,000 to 10,000,000 particles per ml and more preferably between 10,000 and 100,000 particles per ml. A mixing of the sample after adding electrolyte is recommended. Particle diameters should preferably be within 1 to 60 percent of the orifice diameter and more preferably between 5 to 25 percent of the orifice diameter. Volume flow should preferably be from 10 µl to 10 ml per minute and more preferably between 100 µl and 1 ml per minute. For the measurement a constant electrical current of approximately 1 to 5 mA should preferably be applied. The source of electrical current should preferably have a signal to noise ratio (S/N) better than 1,000. The response from the electrode can be filtered electronically by a band-pass filter.

Figure 2:
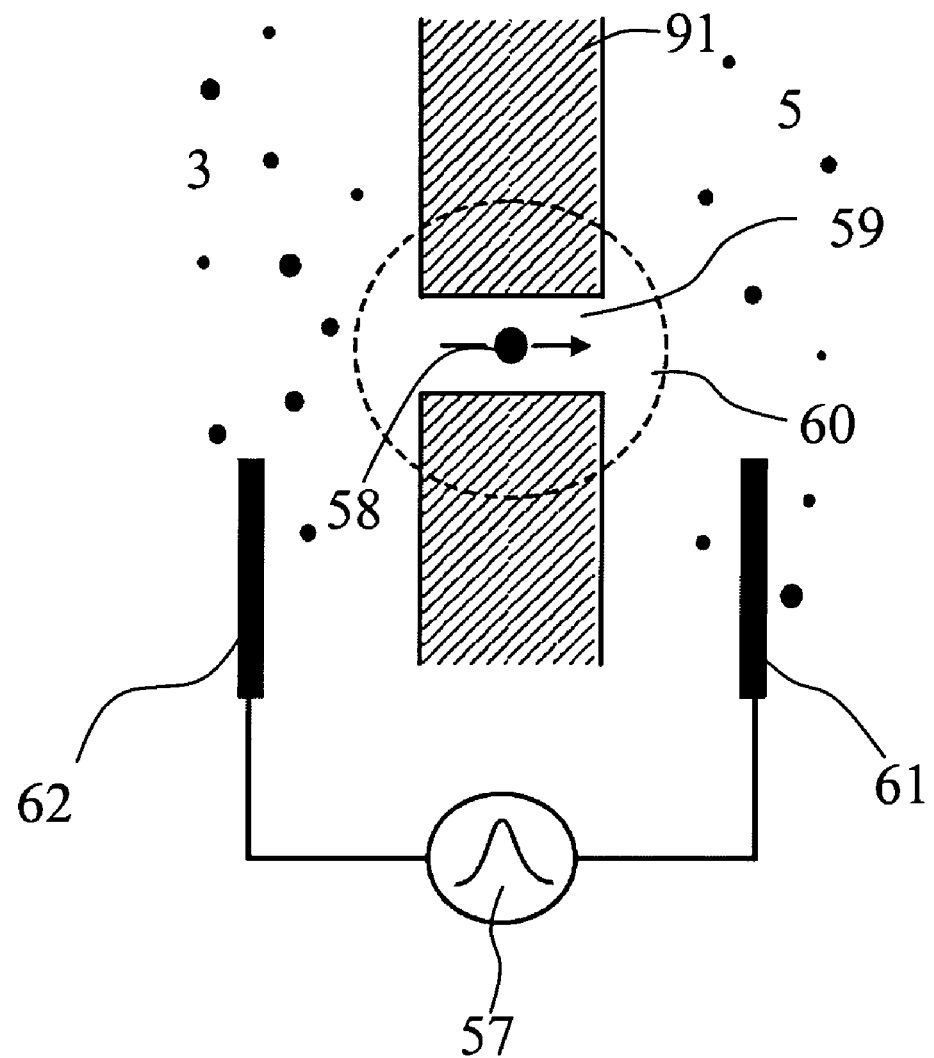
Figure 3:
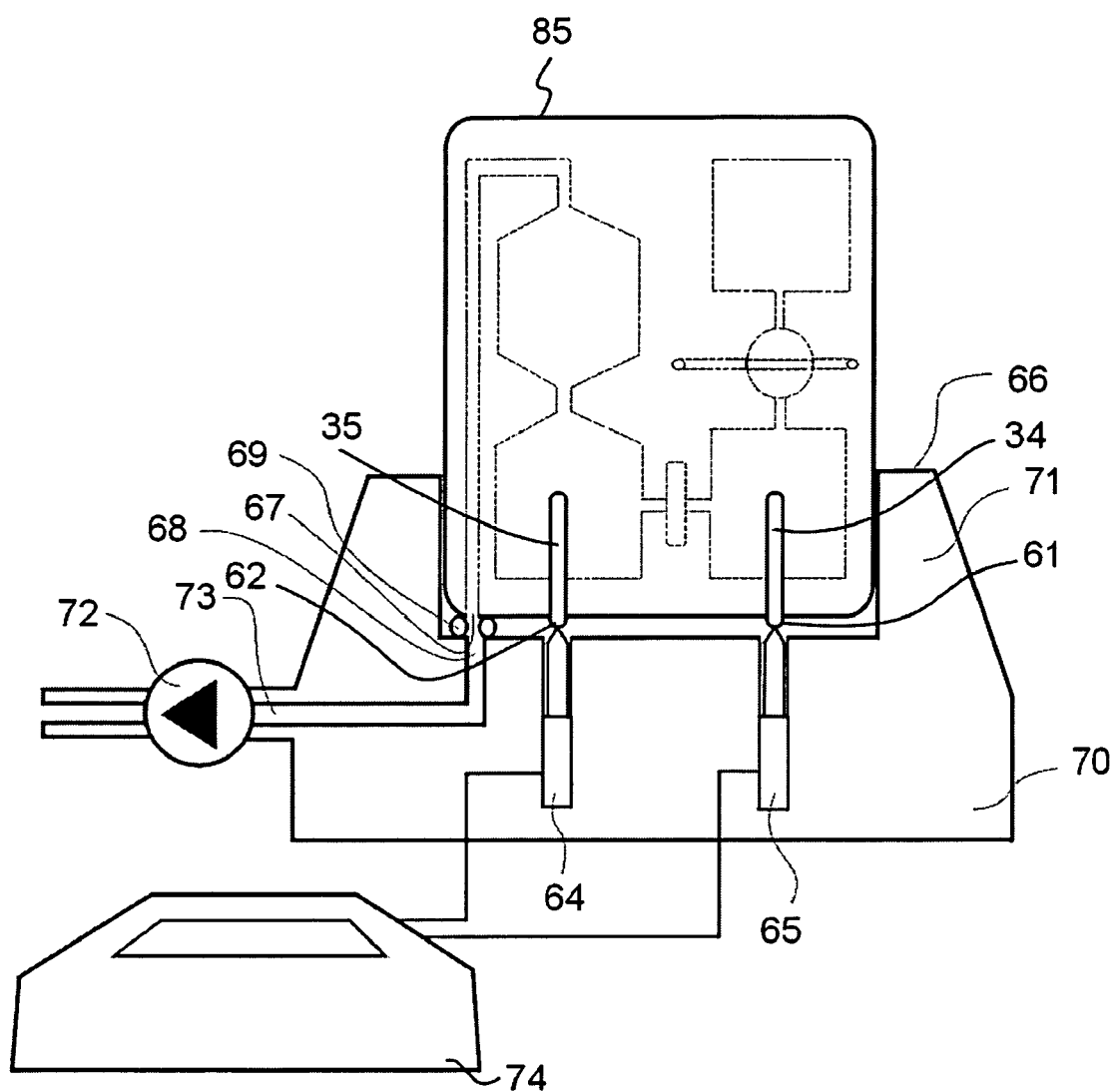
Figure 4:
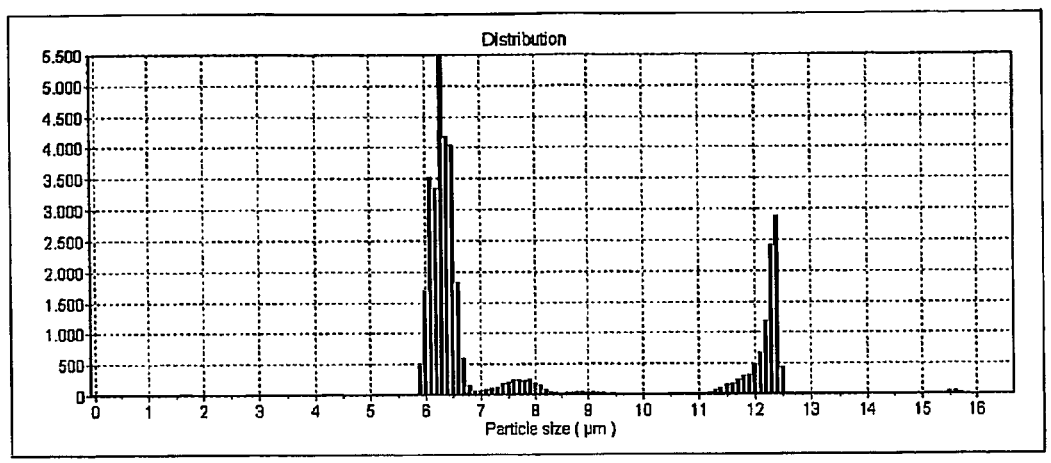
Figure 5:
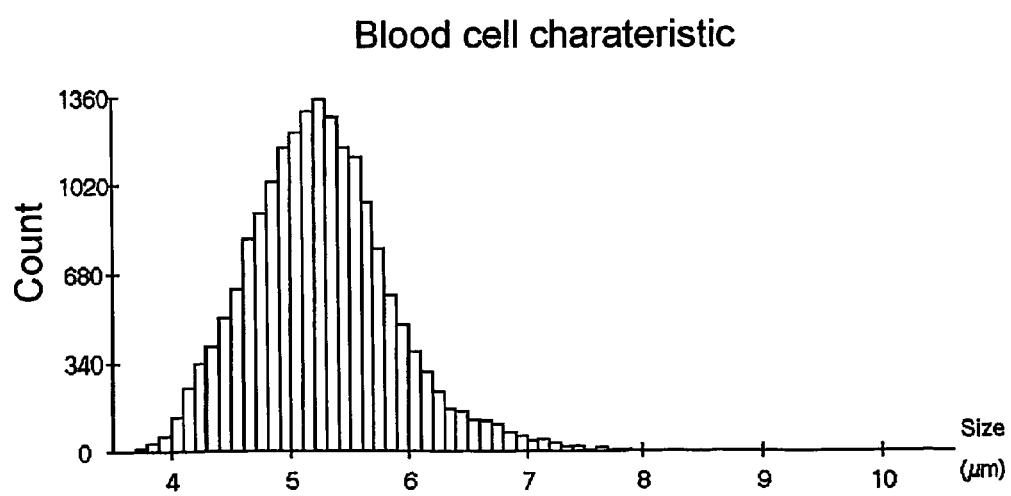
Figure 6:
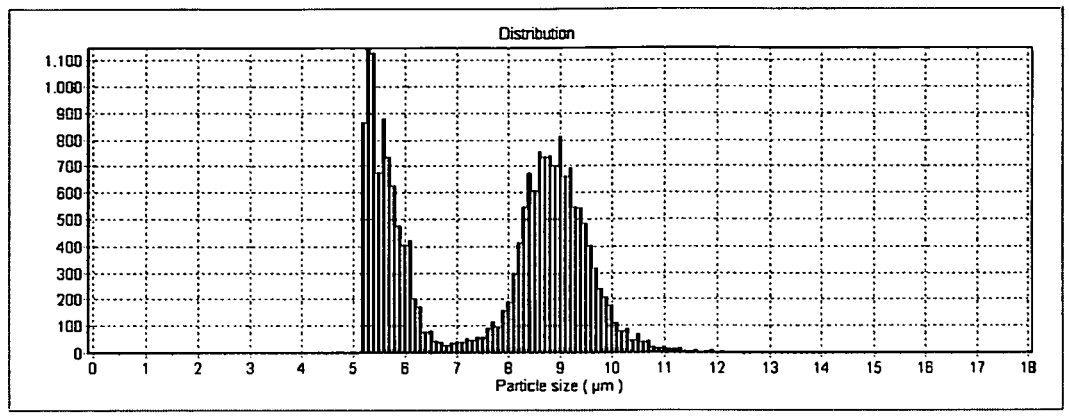
Figure 7:
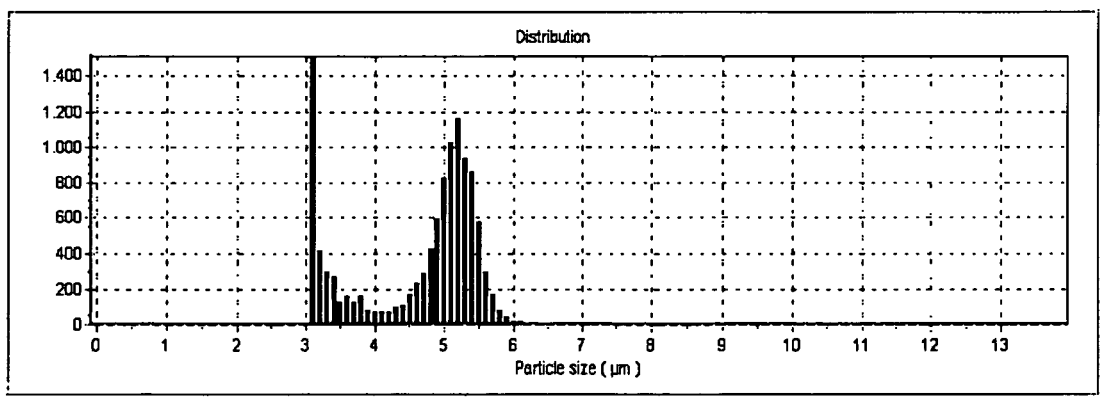
Figure 8:
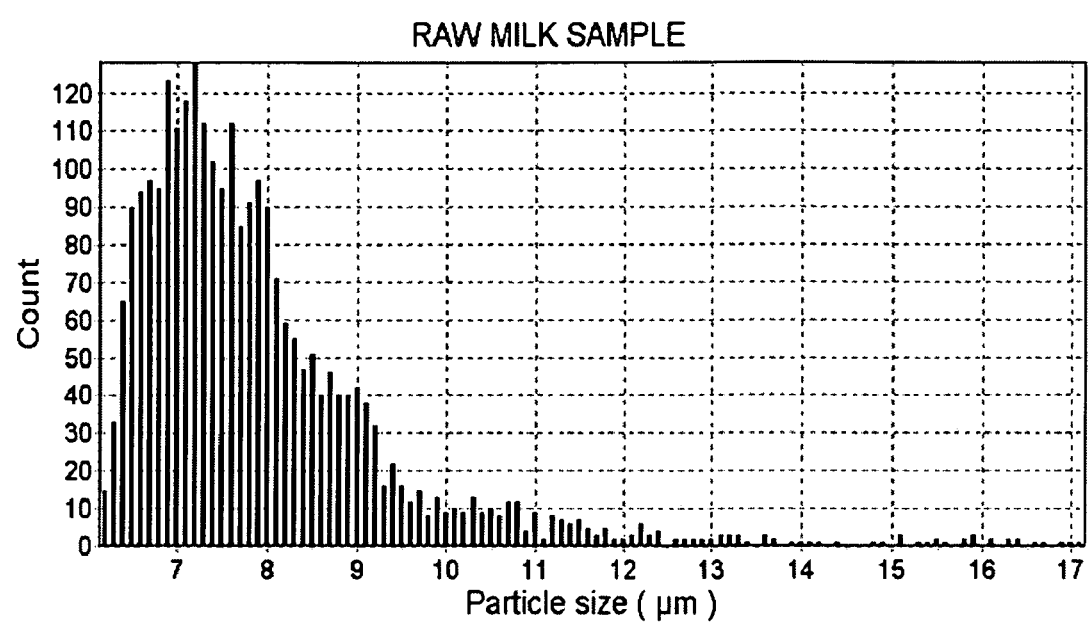
Figure 9:
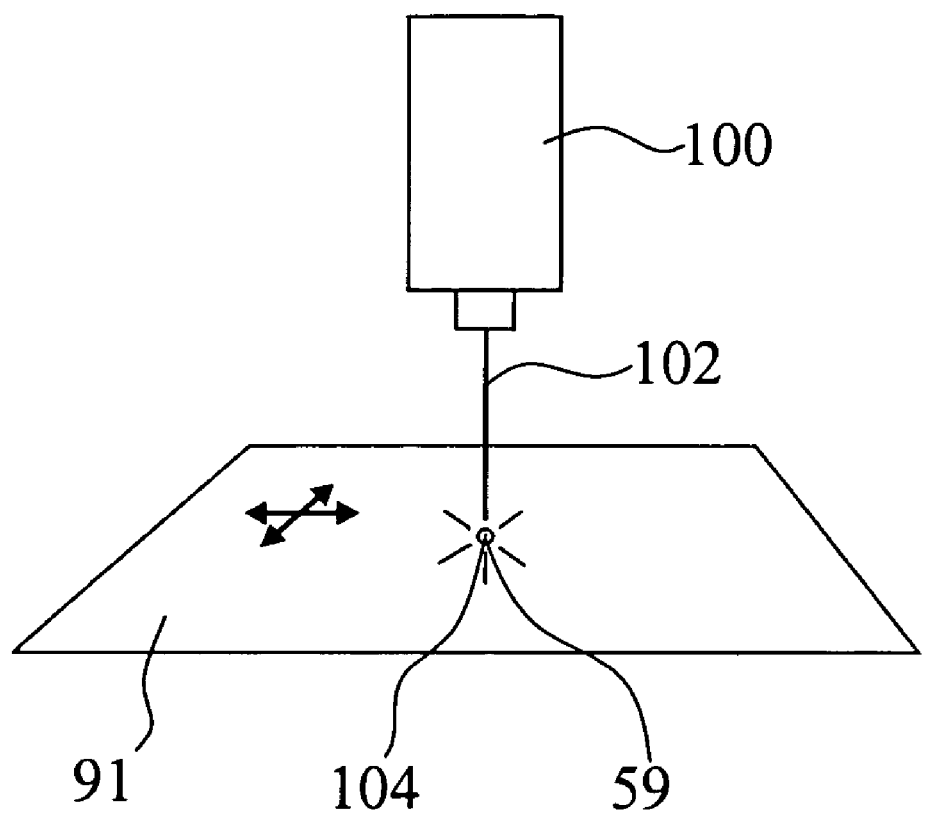
Figure 10:
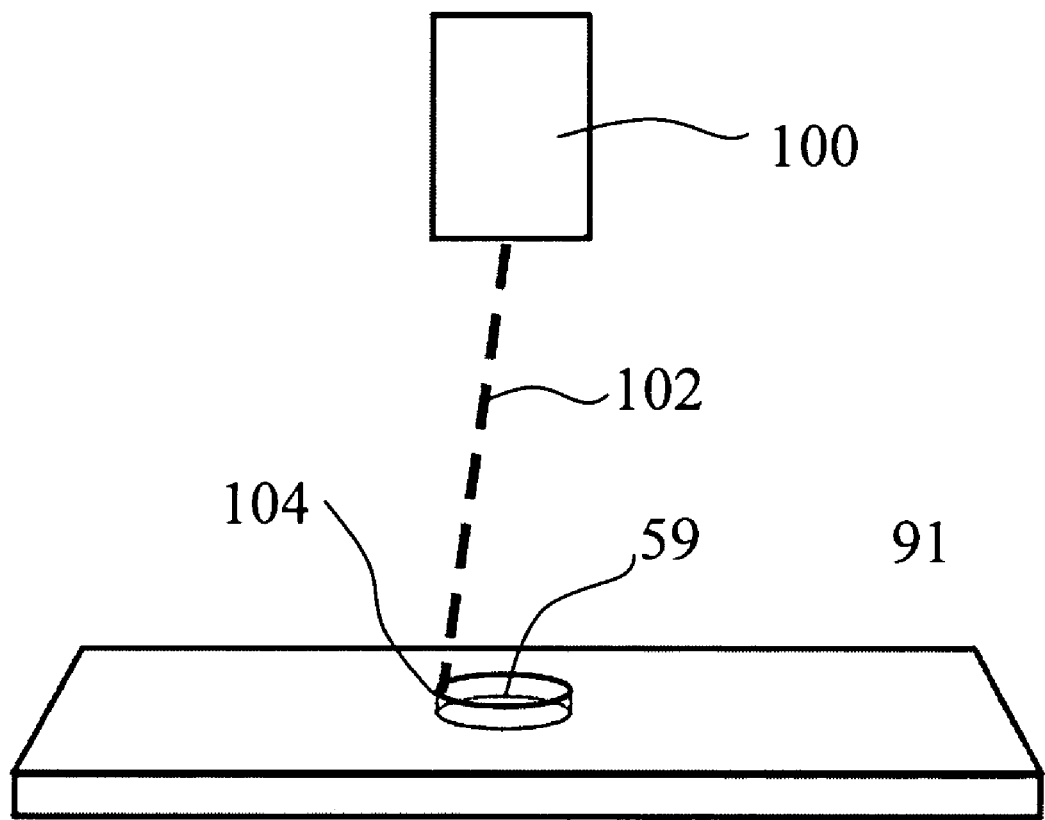
Figure 11:
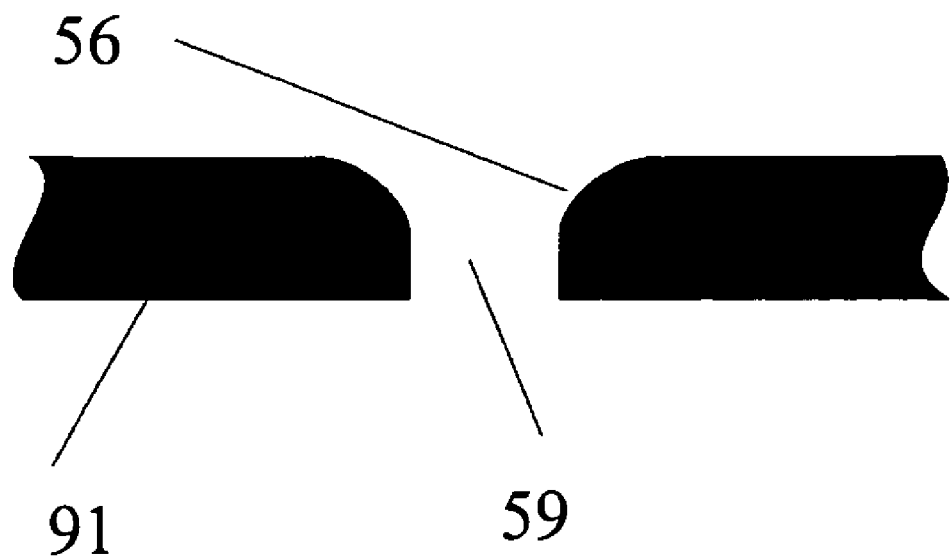

The invention will be further described and illustrated with reference to the accompanying drawings in which:

FIG. 1 is a cross sectional side view through the components of a disposable cartridge according to the present invention, FIG. 2 schematically illustrates the flow-through sensor concept, FIG. 3 schematically illustrates an apparatus according to the present invention with the disposable cartridge, a docking station, and a reader, FIG. 4 is a plot of results obtained in Example 1, FIG. 5 is a plot of results obtained in Example 2, FIG. 6 is a plot of results obtained in Example 3, FIG. 7 is a plot of results obtained in Example 4, FIG. 8 is a plot of results obtained in Example 5, FIG. 9 schematically illustrates manufacturing of a membrane with an orifice according to an embodiment of the present invention, FIG. 10 schematically illustrates manufacturing of a membrane with an orifice according to another embodiment of the present invention, and FIG. 11 shows a cross-section of a membrane orifice manufactured in accordance with the present invention.

FIG. 1 shows a disposable cartridge with a housing 85 for blood analysis, comprising a liquid storage chamber 1 containing a liquid diluent 11, a sampling member 2 positioned in the housing 85 for sampling a blood sample 8 and having a cavity 10 for receiving and holding the blood sample 8, the member 2 being movably positioned in relation to the housing 85 in such a way that, in a first position, the cavity 10 is in communication with a bore 90 for entrance of the blood sample 8 into the cavity 10 by capillary forces, and, in a second position, the cavity 10 is in communication with the liquid storage chamber 1 and a mixing chamber 3 for discharge of the blood sample 8 diluted by the liquid diluent 11 into the mixing chamber 3. The mixing chamber 3 is separated by a membrane according to the present invention with an orifice 59 from and a collection chamber 5 for the passage of the blood sample 8 between the mixing chamber 3 and the collection chamber 5. The membrane containing the orifice 59 constitutes a part of a flow-through sensor 4.

A volume metering arrangement is connected to the collection chamber comprising a volume metering chamber 6 having the size of the volume to be measured during the measurement with two connecting channels 12, 13 of relatively diminutive internal volumes for registering liquid entry and exit by optical or electrical means, from the volume metering chamber a channel 7 leads out to a connection port 67 where a pressure can be applied.

FIG. 2 schematically illustrates counting and sizing of particles by impedance determinations. FIG. 2 shows a cross-section of a part of the membrane 91 containing the orifice 59. Two chambers, the mixing chamber 3 and the collection chamber 5 communicate through the orifice 59. The chambers 3, 5 contain electrodes 61, 62 for generation of an electrical field between them. The membrane 91 is an electrical isolator and thus, the orifice 59 restricts the electrical field whereby a sensing zone 60 is established through which particles 58 are aspirated. In the sensing zone 60, each particle 58 will give rise to a displacement of the surrounding electrolyte, thus blocking part of the current-path between the electrodes 61, 62 thereby generating a short voltage pulse 57. By aspiration of particles, preferably one by one, through the orifice 59, the particles 58 can be characterized with respect to volume and conductivity by registration of the respective voltage pulse 57 characteristics.

FIG. 3 schematically illustrates an apparatus with the disposable cartridge, a docking station and a reader. The chambers on each side of the flow through sensor have electrodes 34, 35 extending from an external terminal 61, 62 through the base wall 63 of the disposable unit and into a configuration facing the inside of its respective chamber. The cartridge is placed in a docking station 66 in a portable apparatus in order to carry out the test. The docking station 66 has a cup shaped housing having a base 70 and a circumambient sidewall 71. In the base 70 there are respective spring loaded electrical connectors 64, 65 for contacting the terminals 61, 62 of the cartridge automatically when the cartridge is received as a push fit into the docking station. There is also a conduit 68 passing through the base wall 70 aligned with the conduit 67 of the cartridge. Conduit 67 at its opening into the upper face of the wall 70 has a seal 69, such as e.g. and O-ring for forming a gas tight connection with the lower face of the base wall 63 of the cartridge. A vacuum pump 72 is connected by a line 73 to the lower end of the conduit 68. In a modification of the apparatus, the vacuum pump 72 can be reversed so as to apply positive gas pressure to the conduit 68.

Schematically indicated at 74 are the further conventional components of a Coulter counter including all the electronic circuitry and display equipment needed for the operation of the apparatus.

FIG. 4

Example 1

Sizing of Polymer Beads

A mixture of 5 μm and 10 μm particles suspended in electrolyte was aspirated through the orifice of the apparatus shown in FIG. 3. The numbers of particles detected and the size of each detected particle were recorded. A bimodal distribution of detected particle size is clearly seen in the figure.

FIG. 5

Example 2

Red Blood Cell Counting

Measurement of blood cells has been performed and the result is shown in FIG. 5. Red blood cells are normally around 5 to 7 μm in diameter and are the most frequent in whole blood, as can be seen on the FIG. 5. The distribution is a Gaussian curve, as it should be expected. Blood counts can be used in clinical diagnostics. It is fairly simple to count erythrocytes, leukocytes and thrombocytes by impedance measurements, which are considered the basic parameters for haematology (see "Fundamentals of Clinical Haematology", Stevens, W.B. Saunders Company, ISBN 0-7216-4177-6).

FIG. 6

Example 3

White Cell Counting Using a Diluent Containing a Reagent-Composition Selected so as to Preserve All Blood Cells Material
  Cartridge and apparatus containing the functions as described in the present invention,
  Isoton, Beckman Coulter (prod. no. 24655) containing: sodium chloride 7.9 g/L, potassium chloride 0.4 g/L, disodiumhydrogenphosphate 1.9 g/l, sodiumdihydrogenphosphate 0.2 g/L, disodium-EDTA 0.4 g/L and sodium fluoride 0.3 g/L.
  Vacutainer, K3E, Becton & Dickinson, prod. No. 367652.
  Bayer, ADVIA-120 equipment.

Performance
  The full sequence of the procedure was as follows:
  Collection of a venous blood sample in a vacutainer tube.
  Leaving the sample, for the sedimentation process to proceed, for three hours.
  Extraction the plasma phase with the major part of the buffy-coat section included
  Performing analysis using the Bayer Advia 120 equipment for obtaining a comparative value for the content of leukocytes.

Adding 5.00 ml isotonic solution as diluent to the chamber of the test rig

Adding 10.0 µl of sample to the chamber

Mixing liquids in the chamber

Starting test sequence on the computer (starts the pump and readies the sampling)

When the liquid reaches the first level electrode sampling is started

When the liquid reaches the second level electrode the sampling is stopped

Sampled values are saved in a file

The file is opened with a "pulse-viewer" for data analysing and calculation of the result using a method of calculation involving subtraction of, with the leukocytes overlapping red blood cells.

Results

Bayer Advia-120: 11.96×10^9 leukocytes/L

Test-rig: 11.92×10^9 leukocytes/L

Difference in accuracy: (11.96−1.92)/11.96=0.33%

FIG. 7

Example 4

White Cell Isolation Using a Diluent Containing a Reagent Composition Selected so as to Primarily Hemolyse the Red Blood Cells Material Cartridge and apparatus containing the functions as described in the present invention, Diluent containing: procaine hydrochloride 0.10 g/L, 1,3-dimethylolurea 0.90 g/L, N-(1-acetamido)iminodiacetic acid 1.28 g/L, dodecyltrimethyl ammonium chloride 7.51 g/L and sodium chloride 0.03 g/L.

Vacutainer, K3EDTA, Becton & Dickinson, prod. No. 367652.

Performance

The full sequence of the procedure was as follows:

Collection of a venous blood sample in a vacutainer tube.

Leaving the sample, for the sedimentation process to proceed, for three hours.

Extraction the plasma phase with the major part of the buffy-coat section included Adding 2,000 ml diluent as described above to the chamber of the test rig Adding 4.0 µl of sample to the chamber Mixing liquids in the chamber Starting test sequence on the computer (starts the pump and readies the sampling)

When the liquid reaches the first level electrode sampling is started

When the liquid reaches the second level electrode the sampling is stopped

Sampled values are saved in a file

The file is opened with a "pulse-viewer" for data analysing and generation of the result.

Results

As can be seen in the histogram in FIG. 6 the particle population corresponding to the leukocytes is easily identified in the absence of the red blood cells.

FIG. 8

Example 5

Counting Somatic Cells

Milk quality is essential for farmers, diary producers and consumers. Farmer has to deliver milk of a certain quality, which is controlled by the so-called Somatic Cell Count (SCC). In milk quality tests somatic cells in the milk are counted to determine infections (clinical mastitis). A limit of 400,000 cells pr. ml. has to be met by the farmers for dairy resale. Change of diet, stress or mastitis lead to higher SCC levels, thus lowering the quality of the milk and consequently lowering the price per unit volume. A cheap cell counter will help farmers and diary producers monitor SCC-level.

As schematically illustrated in FIG. 9, orifices 59 for Impedance cell sizing can be fabricated by laser micro machining of polymers 91 leading to a simple and convenient way of fabricating and assembling orifices 59 for the cartridge. A series of small orifices of 50 µm has been fabricated with an UV-laser 100. The orifices 59 are made in less than 10 ms in a 50 µm polymer sheet. The uniformity of the orifices 59 is very high and the smoothness of the orifice entrance is unique.

Preferably, the laser 100 is a UV-laser, such as an excimer laser with a wavelength in the range from 150 nm to 350 nm, because of its superior laser cutting accuracy.

Manufacturing of polymer membranes 91 with orifices 59 by laser cutting according to the present invention provides cheap and rapid production of membranes 91 with precision-machined orifices 59 for impedance particle counting and/or sizing.

The high-energy laser spot 104 causes vaporization or ablation of the material in the focused region of the spot 104. The laser spot 104 of an excimer laser 100 may be focused to a few micrometers, providing the desired accuracy in accordance with the present invention.

In the embodiment illustrated in FIG. 9, the laser 100 is used like a conventional drill, i.e. the focussed laser spot 104 remains at the desired position of the orifice and the orifice 59 is produced by a series of laser pulses.

In the embodiment illustrated in FIG. 10, the focussed laser beam 102 is scanned along the desired circumference of the orifice 59 thereby cutting-out the orifice 59 of the membrane 91. In this way any desired circumferential shape of the orifice 59 may be manufactured.

According to yet another embodiment of the invention, a narrow laser beam 102 is scanned for example linearly, e.g. line by line, across the surface of the membrane 91 desired to be removed for creation of the orifice 59.

FIG. 11 shows a cross-section of a membrane orifice 59 manufactured in accordance with the present invention. The illustrated polymer membrane 91 is provided with an orifice 59 with rounded edges 56 at one of the sides of the membrane 91 whereby perturbations of an electrical field at the orifice 59 entrance are minimised and a substantially homogenous electrical field at the centre of the orifice 59 may be provided.

Hereby, electrical pulses generated by particles passing the orifice 59 at the centre of the orifice 59 and particles passing the orifice 59 close to an edge of the orifice 59 will generate substantially identical pulses. Without rounded edges 56, particles passing the orifice 59 close to an edge will generate a distorted pulse.

Preferably, the radius of curvature of the rounded edges 56 corresponds to ¼th the diameter of the orifice 59.

The invention claimed is:

1. An electrical impedance cell counting apparatus for counting and characterizing particles suspended in a liquid, comprising:
   a housing with a mixing chamber and a collection chamber separated by a polymer membrane containing an orifice for passage of the particles between the mixing chamber and the collection chamber, wherein a diameter of the orifice is in a range from 10 µm to 1,000 µm;
   electrodes within the mixing and collection chambers configured to provide pulses by impedance determination for counting the particles that pass through the orifice; and
   a volume meter that determines a period during which a fixed volume of the liquid passes through the orifice.

2. An electrical impedance cell counting apparatus according to claim 1, wherein the orifice has rounded edges at one of the sides of the membrane whereby perturbations of an electrical field at an orifice entrance are minimized and a substantially homogenous electrical field at the center of the orifice is provided.

3. An electrical impedance cell counting apparatus according to claim 2, wherein a radius of curvature of the rounded edges is substantially equal to $1/4^{th}$ the diameter of the orifice.

4. An electrical impedance cell counting apparatus according to claim 1, wherein a surface roughness of an internal surface of the orifice is in a range from 0 µm to 5 µm, whereby a substantially homogenous electrical field at a center of the orifice is provided.

5. An electrical impedance cell counting apparatus according to claim 1, wherein the orifice diameter is in a range from 30 µm to 75 µm.

6. An electrical impedance cell counting apparatus according to claim 1, wherein the orifice diameter is 50 µm.

7. An electrical impedance cell counting apparatus according to claim 1, wherein a length of the orifice ranges from 1 µm to 1000 µm.

8. An electrical impedance cell counting apparatus according to claim 1, wherein the membrane is positioned in a single-use cartridge.

9. An electrical impedance cell counting apparatus according to claim 1, further comprising:
   a bore in an outer surface of the housing for entrance of a liquid sample, communicating with
   a sampling member positioned in the housing for sampling the liquid sample and having a cavity for receiving and holding the liquid sample, the sampling member being movably positioned in relation to the housing in such a way that in a first position the cavity is in communication with the bore for entrance of the liquid sample into the cavity, and in a second position the cavity is in communication with the mixing chamber for discharge of the liquid sample into the mixing chamber.

10. An electrical impedance cell counting apparatus according to claim 1, wherein deviation of the orifice diameter along a longitudinal axis of the orifice ranges from +/−1% to +/−10%, whereby a substantially homogenous electrical field is provided at a center of the orifice.

11. An electrical impedance cell counting apparatus according to claim 1, wherein a largest cross-sectional dimension of the orifice is from 10 µm to 50 µm.

12. An electrical impedance cell counting apparatus according to claim 1, wherein the volume meter comprises:
   a volume metering chamber having an entrance connected to the collection chamber, and having a detector that detects liquid at the entrance and at an exit of the volume metering chamber.

13. An electrical impedance cell counting apparatus according to claim 12, wherein the detector comprises an optical detector.

14. An electrical impedance cell counting apparatus according to claim 12, wherein the detector comprises an electrical detector.

15. An electrical impedance cell counting apparatus for counting and characterizing particles suspended in a liquid, comprising:
   a housing with a mixing chamber and a collection chamber separated by a polymer membrane containing an orifice for passage of the particles between the mixing chamber and the collection chamber; and
   electrodes within the mixing and collection chambers configured to provide pulses by impedance determination for counting the particles that pass through the orifice,
   wherein a diameter of the orifice is in a range from 10 µm to 1,000 µm, and wherein a diameter of the particles is not greater than 60 percent of the diameter of the orifice.

16. An electrical impedance cell counting apparatus according to claim 15, wherein the orifice has rounded edges at one of the sides of the membrane whereby perturbations of an electrical field at an orifice entrance are minimized and a substantially homogenous electrical field at the center of the orifice is provided.

17. An electrical impedance cell counting apparatus according to claim 16, wherein a radius of curvature of the rounded edges is substantially equal to $1/4^{th}$ the diameter of the orifice.

18. An electrical impedance cell counting apparatus according to claim 15, wherein a surface roughness of an internal surface of the orifice is in a range from 0 µm to 5 µm, whereby a substantially homogenous electrical field at a center of the orifice is provided.

19. An electrical impedance cell counting apparatus according to claim 15, wherein the membrane is positioned in a single-use cartridge.

20. An electrical impedance cell counting apparatus according to claim 15, further comprising:
   a bore in an outer surface of the housing for entrance of a liquid sample, communicating with
   a sampling member positioned in the housing for sampling the liquid sample and having a cavity for receiving and holding the liquid sample, the sampling member being movably positioned in relation to the housing in such a way that in a first position the cavity is in communication with the bore for entrance of the liquid sample into the cavity, and in a second position the cavity is in communication with the mixing chamber for discharge of the liquid sample into the mixing chamber.

21. An electrical impedance cell counting apparatus of claim 15, wherein the diameter of the particles is between 5 to 25 percent of the diameter of the orifice.

22. An electrical impedance cell counting apparatus of claim 15, further comprising a volume meter that determines a period during which a fixed volume of the liquid passes through the orifice.

23. An electrical impedance cell counting apparatus according to claim 15, wherein the volume meter comprises:
   a volume metering chamber having an entrance connected to the collection chamber, and having a detector that detects liquid at the entrance and at an exit of the volume metering chamber.

24. An electrical impedance cell counting apparatus according to claim 23, wherein the detector comprises an optical detector.

25. An electrical impedance cell counting apparatus according to claim 23, wherein the detector comprises an electrical detector.

26. A single-use disposable electrical impedance cell counting cartridge for counting and characterizing particles suspended in a liquid, comprising a housing with a mixing chamber and a collection chamber separated by a polymer membrane containing an orifice for passage of the particles between the mixing chamber and the collection chamber for impedance determination of the particles, wherein a diameter of the orifice is in a range from 10 µm to 1,000 µm.

27. A single-use disposable electrical impedance cell counting cartridge of claim 26, further comprising a volume meter for determining a beginning and an end of a period during which a fixed volume of the liquid passes through the orifice.

28. A single-use disposable electrical impedance cell counting cartridge of claim 27, wherein the volume meter comprises:

a volume metering chamber having an entrance connected to the collection chamber, and having an exit, wherein the entrance and the exit of the volume metering chamber are configured for detecting presence of the liquid at the entrance and at the exit.

29. A single-use disposable electrical impedance cell counting cartridge of claim 27, further comprising electrodes within the mixing and collection chambers configured to provide pulses by impedance determination for counting the particles that pass through the orifice.

* * * * *